United States Patent [19]

Shibano et al.

[11] Patent Number: 5,399,483
[45] Date of Patent: Mar. 21, 1995

[54] EXPRESSION OF MDR-RELATED GENE IN YEAST CELL

[75] Inventors: Yuji Shibano, Osaka; Kazumitsu Ueda; Tohru Komano, both of Kyoto, all of Japan

[73] Assignee: Suntory Limited, Osaka, Japan

[21] Appl. No.: 978,442

[22] Filed: Nov. 18, 1992

Related U.S. Application Data

[63] Continuation of Ser. No. 613,715, Nov. 30, 1990, abandoned.

[30] Foreign Application Priority Data

Mar. 30, 1989 [JP] Japan .................... 1-80188

[51] Int. Cl.⁶ .................... C12Q 1/02; C12N 1/19
[52] U.S. Cl. .................... 435/7.31; 435/254.21; 435/317.1
[58] Field of Search .................... 435/69.1, 172.1, 256, 435/320.1, 254.21, 7.31, 317.1; 935/22, 28, 33, 37, 66, 69

[56] References Cited

U.S. PATENT DOCUMENTS 4,912,039 3/1970 Riordan .................... 435/69.1

FOREIGN PATENT DOCUMENTS 63-245664 10/1988 Japan .................... C12N 1/16
8705943 10/1987 WIPO .................... C12Q 1/68

OTHER PUBLICATIONS

Tschopp et al., *J. Bact.*, vol. 156, 1983, pp. 222–229.
Kelley et al., "Isolation and characterization of a λpolA tranducing phage", Proc. Natl. Acad. Sci. USA, vol. 74, No. 12, pp. 5632–5636, Dec. 1977, Genetics; see p. 5635, second paragraph, left column.
Fujita et al., "Biosynthesis of the Torpedo California Acetylcholine Receptor α Subunit in Yeast", Science, vol. 231, pp. 1284–1287; see p. 1286, left upper col., lines 5–10, (1986).
Safa et al., "Identification of the Multidrug Resistance–related Membrane Glycoprotein as an Acceptor for Calcium Channel Blockers", JBC 262(16):7884–7888 (Jun. 1987).
Udda et al., "The *mdrl* gene, responsible for multidrug resistance, codes for P-glycoprotein", Biochem. Biophys. Res. 141(3):956–962 (Dec. 1986).
Gros et al., "Mammalian Multidrug Resistance Gene: Complete cDNA sequence Indicates Strong Homology to Bacterial Transport Proteins", Cell 47:371–380 (Nov. 1986).

*Primary Examiner*—Richard A. Schwartz
*Assistant Examiner*—James Kettar
*Attorney, Agent, or Firm*—Cushman Darby & Cushman

[57] ABSTRACT

A yeast host which can express P-glycoprotein, i.e., the product of MDR-related gene, in the cell membrane in the same state as observed in multidrug resistant cells produced by connecting the MDR-related gene which carries multidrug resistance to a yeast expression vector and transforming the yeast with said recombinant vector; a cell membrane fraction containing a substantial amount of P-glycoprotein produced by said yeast and a process for the preparation thereof; and a recombinant vector for expressing the MDR-related gene in a yeast host.

8 Claims, 6 Drawing Sheets

1. G-1315(pYM1), BH LOW MEDIUM, MEMBRANE FRACTION
2. G-1315(pYM1), BH LOW MEDIUM, CYTOPLASM FRACTION
3. G-1315(pYM1), BH HIGH MEDIUM, MEMBRANE FRACTION
4. G-1315(pYM1), BH HIGH MEDIUM, CYTOPLASM FRACTION
5. G-1315(pYM2), BH LOW MEDIUM, MEMBRANE FRACTION
6. G-1315(pYM2), BH LOW MEDIUM, CYTOPLASM FRACTION
7. G-1315(pYM2), BH HIGH MEDIUM, MEMBRANE FRACTION
8. G-1315(pYM2), BH HIGH MEDIUM, CYTOPLASM FRACTION
9. G-1315, BH HIGH MEDIUM, MEMBRANE FRACTION
10. G-1315, BH HIGH MEDIUM, MEMBRANE FRACTION

Fig. 3

1. G-1315(pYM1), BH LOW MEDIUM
2. G-1315(pYM1), BH HIGH MEDIUM
3. G-1315, BH LOW MEDIUM
4. G-1315, BH HIGH MEDIUM

Fig. 4

1. NONE
2. VERAPAMIL
3. VINBLASTIN
4. COLCHICINE

Fig. 5

EXPRESSION OF MDR-RELATED GENE IN YEAST CELL

This is a contination of application Ser. No. 07/613,715, filed on Nov. 30, 1990, abandoned.

BACKGROUND OF THE INVENTION

1. Field of the Invention

This invention relates to transformed yeast cells having P-glycoprotein accumulated at the cell membrane in a similar manner as in human multidrug resistant cells, P-glycoprotein produced and accumulated at the cell membrane of said yeast cells and a recombinant vector to be used for the expression of said P-glycoprotein from a multidrug resistance-related gene (MDR-related gene).

Prior Arts

It is frequently observed in the chemotherapy of cancer that an antitumor agent, which is effective in the early stages of the treatment, loses its effect when the treatment is repeated. This is partly caused by a change in cancer cells. Namely, the acquisition of drug resistance by cancer cells is a serious problem. In the relapse or metastasis of a cancer, in particular, cancer cells would frequently acquire a resistance against a number of various antitumor agents. This multidrug resistance (MDR) is a serious obstacle to chemotherapy of cancer. Since early 1970's, many researchers have studied the multidrug resistance by using, for example, cultivated mouse, hamster and human cells. Known multidrug resistant cells have common characteristics as follows: (1) simultaneously show resistance against many different antitumor agents which are not in common in functional point or structure; (2) show an elevated rate at which a drug is excreted out of the cells; (3) the excretion of a drug is inhibited by metabolic inhibitors; and (4) show an increased expression of membrane glycoprotein (P-glycoprotein) of a molecular weight of approximately 170 kd. These facts suggested that the multidrug resistance might be contained in a single gene or two or more genes closely related to each other and that one such gene might code P-glycoprotein so as to act as an energy-dependent pump for excreting drugs [Pastan, I., et al., N. Eng. J. Med., 316, 1388 (1987)].

Since gene amplification was observed in multidrug resistant cells, a certain DNA sequence amplified in multidrug resistant cells was isolated [Roninson, I. B. et al., Proc. Natl. Acad. Sci. USA, 83, 4538 (1986)]. By using the DNA sequence thus isolated as a probe, the full-length cDNA of MDR1 gene responsible for the aquired multidrug resistance of human cultured cells was isolated from multidrug resistant human KB cells [Ueda, K. et al., J. Biol. Chem., 262, 505 (1987)]. This gene was found to be amplified almost in proportion to the level of drug resistance and expressed as the mRNA.

Figure 5:
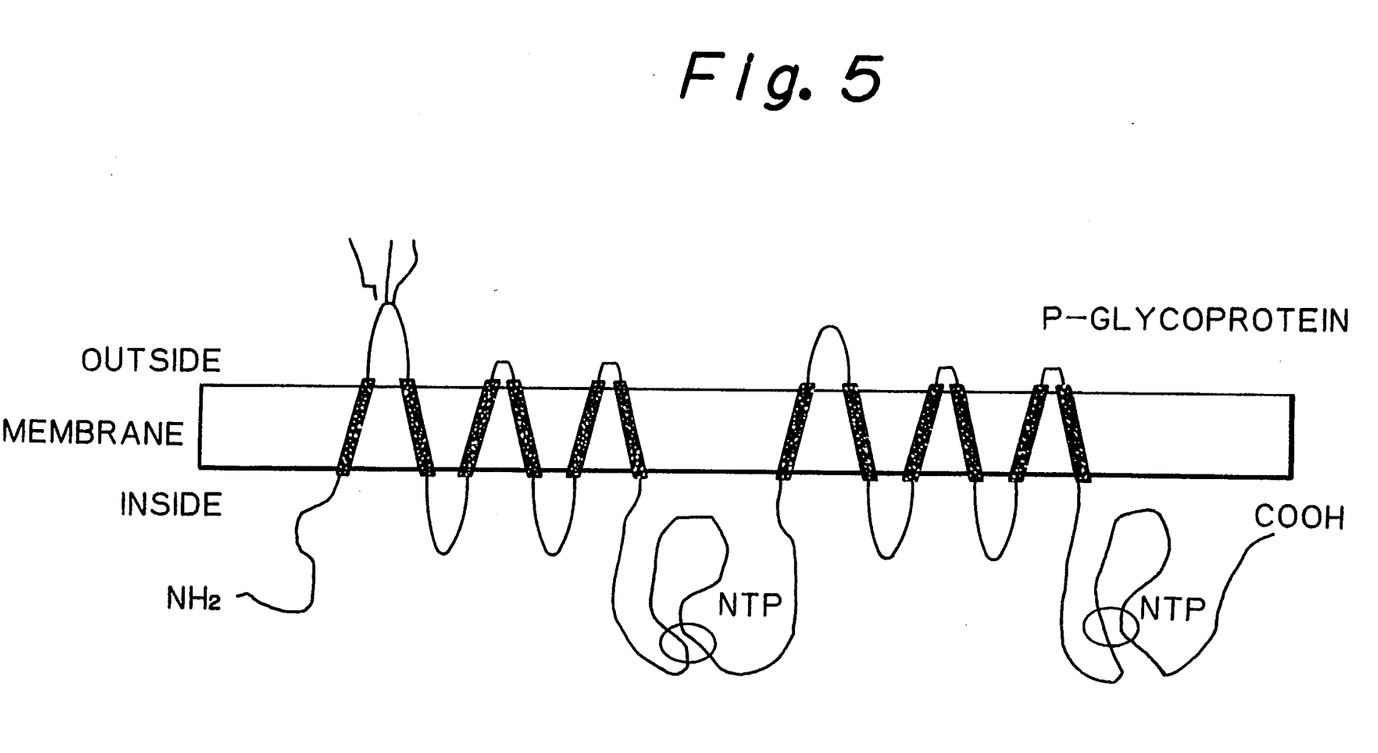
FIG. 5 is an illustration of the assumed integration of P-glycoprotein with the cell membrane.

The full-length MDR1 cDNA thus isolated was connected to the downstream of a strong promoter and then introduced into a strain of a drug-sensitive cell (hereinafter referred to simply as a sensitive cell). As a result, the sensitive cell aqcuired multidrug resistance, which demonstrated that the isolated gene was actually responsible for the multidrug resistance [Ueda, K. et al., Proc. Natl. Acad. Sci. USA, 84, 3004 (1987)]. Further, it has been reported that the product of MDR1 gene is P-glycoprotein per se [Ueda, K. et al., Biochem. Biophys. Res. Commun., 141, 956 (1986); Japanese Patent Domestic Announcement No. 500480/1989]. According to this report, the P-glycoprotein expressed by MDR1 gene in human cells is present being integrated with the cell membrane. Ueda et al. proposed a schematic illustration thereof as shown in FIG. 5. Referring to FIG. 5, P-glycoprotein is integrated with the cell membrane and accumulated thereat in such a manner that the peptide chain of the protein stitches the cell membrane. It is believed that the portion of the P-glycoprotein present in the inside of the cell comprises a nucleotide-binding site, which is referred to by NTP in FIG. 5, exhibits the major role in the energy-dependent excretion pump.

It is highly important in cancer chemotherapy to overcome the multidrug resistance of cancer cells.

In order to overcome the problem of the multidrug resistance so as to improve the treatment of a cancer, it is an urgent need to provide a method which serves as a model system of multidrug resistant cells in a substantial amount, and to provide an antibody capable of specifically recognizing multidrug resistant cells. (In particular, a monoclonal antibody capable of recognizing the exracellular part of P-glycoprotein would be highly effective in evaluating the drug resistance of cancer cells and in overcoming the drug resistance.) It is expected that the solution of said need would make it possible to develop, for example, a process for screening antitumor agents which could overcome the multidrug resistance by using the model system thus obtained, a method of evaluating the level of multidrug resistance of cancer cells by using an antibody to P-glycoprotein and a method of suppressing the multidrug resistance by inhibiting the function of P-glycoprotein by the specific antibody.

Among these objects, it would theoretically be possible to prepare multidrug resistant cells by the method proposed by Ueda et al. [Proc. Natl. Acad. Sci. USA, 84, 3004 (1987), supra] for the preparation of a multidrug resistance model system or to prepare a cell membrane fraction containing P-glycoprotein from said cells. However, preparing such multidrug resistant animal cells in a substantial amount would require a time consuming laborious work and a great amount of cost, since animal cells generally have a low growth rate resulting a low cell density and, furthermore, the cultivation thereof would not be easy.

On the other hand, there has been no known antibody to P-glycoprotein except monoclonal antibody C219 capable of recognizing the intracellular peptide portion of P-glycoprotein [Kartner, N. et al., Nature, 316, 820–823 (1985)] and monoclonal antibody MRK16 capable of recognizing the extracellular moiety of P-glycoprotein [Sugawara, I. et al., Cancer Res., 48, 1926–1929 (1988)]. Monoclonal antibody C216, which recognized the moiety of P-glycoprotein located inside the cell membrane, is unsuitable for overcoming the multidrug resistance or evaluating the drug resistance level of cancer cells. On the other hand, MRK16, which recognizes the extracellular moiety of P-glycoprotein, has disadvantages in that the sensitivity of this antibody in detecting P-glycoprotein is low. Thus none of these known antibodies is satisfactory for achieving the aforesaid objects.

Thus no practical antibody to P-glycoprotein has been available hitherto. This could be accounted for by the fact that drug-resistant cells or a membrane fraction prepared therefrom is required as an antigen for the production of such an antibody. However, it is difficult to grow animal cells on a large scale, as described above. Furthermore, animal cells have, in general, various proteins and sugar chains and, therefore, a number of antigen determinants on the surface layer thereof, which makes the screening of the target monoclonal antibody difficult.

SUMMARY OF THE INVENTION

The present inventors have successfully engineered transformed yeasts capable of expressing a substantial amount of P-glycoprotein, which is an MDR-related gene product, by connecting an MDR-related gene which carries multidrug resistance to an expression vector of yeasts and then transforming the yeast with said recombinant plasmid. Furthermore, they have surprisingly found that P-glycoprotein expressed in said transformed yeast is accumulated in the cell membrane of the yeast.

Accordingly, the present invention aims at providing an MDR-related gene expression yeast wherein P-glycoprotein is expressed at the cell membrane in the same manner as the one observed in human drug resistant cells, a cell membrane fraction from said yeast containing a substantial amount of P-glycoprotein and a process for the preparation of said membrane fraction to thereby enable access to a model system which mimics multidrug resistant cells and to prepare an antibody specific to multidrug resistant cells.

Furthermore, the present invention aims at providing a recombinant vector for the expression of the aforesaid MDR-related gene in yeast.

DETAILED DESCRIPTION OF THE INVENTION

In order to prepare the transformed yeast cells of the present invention, an MDR-related gene is employed. The term "MDR-related gene" as used herein generally refers to genetic coding for P-glycoproteins which are derived either from humans or animals and are responsible for multidrug resistance as well as genetic coding for proteins having substantially the same characteristics in terms of multidrug resistance. For example, MDR1 gene, which has been isolated from multidrug resistant cells derived from human KB cells by the selection in the presence of colchicine [Ueda K. et al., J. Biol. Chem., 262, 505 (1987)], is particularly useful in the present invention. Further, it has been reported that a gene closely related to MDR gene is present in human normal cells as well as in cancer cells which are seemingly nonmultidrug resistant. The results of northern hybridization of mRNA preparations extracted from normal human tissues indicated that this gene is tissue-specifically expressed [Fojo, A. T., Proc. Natl. Acad. Sci. USA, 84, 265 (1987)]. For example, it shows intense expression in the adrenal glands, kidney, colon, liver, jejunum and rectum. A study with the use of an antibody has indicated that P-glycoprotein formed by the expression distributes on the surface of the epithelial cells of liver, kidney, pancreas and small intestine [Thiebaut, F. et al., Proc. Natl. Acad. Sci. USA, 84, 7735 (1987)]. As one such MDR-related gene, the present inventors cloned MDRA1 gene from human adrenal and clarified the structure thereof. As a result, it has been confirmed that the P-glycoprotein expressed in the normal cells is the same as the P-glycoprotein expressed in drug resistant cells except that two amino acids of the former differ from those of the latter (Japanese Patent Application No. 251475/1988). Accordingly, MDRA1 gene and the like genes isolated from human adrenal or other appropriate tissues are also available in the present invention as MDR-related genes. Similarly, the term "P-glycoprotein" as used herein includes proteins corresponding to any MDR-related genes.

As a promoter required for the expression of MDR-related gene in yeast, any promoter may be used so long as it can exert its function in a yeast. For example, glyceraldehyde 3-phosphate dehydrogenase promoter (GAP) may be used as a promoter of constitutive expression, while acid phosphatase promoter (PHO5) may be used as a promoter for inducive expression. These promoters are disclosed in Japanese Patent Laid-Open No. 141888/1986. On the other hand, any appropriate vectors such as YEp, YCp and YIp may be used as a vector for introducing MDR-related gene into yeast cells. Although the yeast to be used as a host is not specifically restricted, those belonging to the genus *Saccharomyces* may be preferably used. In particular, any strain belonging to *Saccharomyces cerevisiae* may be selected therefor.

MDR-related gene may be inserted into the yeast expression vector by a suitable method known in the field of genetic engineering. For example, restriction sites, which correspond to the restriction sites of the expression vector, are prepared immediately before the initiator codon of MDR-related gene and after the terminator codon thereof. The restriction sites may be prepared by a site-specific mutagenesis method, for example, the one reported by Kunkel [Kunkel, T. A., Proc. Natl. Acad. Sci. USA, 82, 488 (1985)]. Then a DNA fragment including the full length of MDR-related gene is excised at the restriction sites prepared above and the excised gene is inserted into the yeast expression vector. The recombinant plasmid thus obtained is used to transform yeast cells in accordance with a method reported by Ito et al. [Ito H. et al., J. Bacteriol., 153, 163 (1983)] and the transformant is selected with an appropriate marker.

The expression of MDR-related gene in the transformed yeast may be examined by an antibody to P-glycoprotein, for example, monoclonal antibody C219 marketed by Centocor Co. in the following manner. Cultured transformed yeast cells are processed into protoplasts which are then subjected to lysis and centrifuged to give a cell membrane fraction. The resulting cell membrane fraction is subjected to polyacrylamide gel electrophoresis in the presence of SDS to separate proteins. Next, the protein band reacting with monoclonal antibody C219 is detected by western blotting technique. Further, the $^3$H-azidopine binding assay [Safa et al., J. Biol. Chem., 262, 7884 (1987)] may be performed by using the membrane fraction thus obtained in order to determine the bindability of the drug to the P-glycoprotein. The results of such an assay will be useful in developing antagonists for multidrug resistance. That is, various drugs may be added to the assay mixture upon the reaction between P-glycoprotein with the azidopine. When one of these drugs inhibits the binding between P-glycoprotein and azidoplne, this drug may be regarded as a multidrug resistance antagonist.

To further illustrate the present invention, the following Examples will be given.

Example 1

Figure 1A:
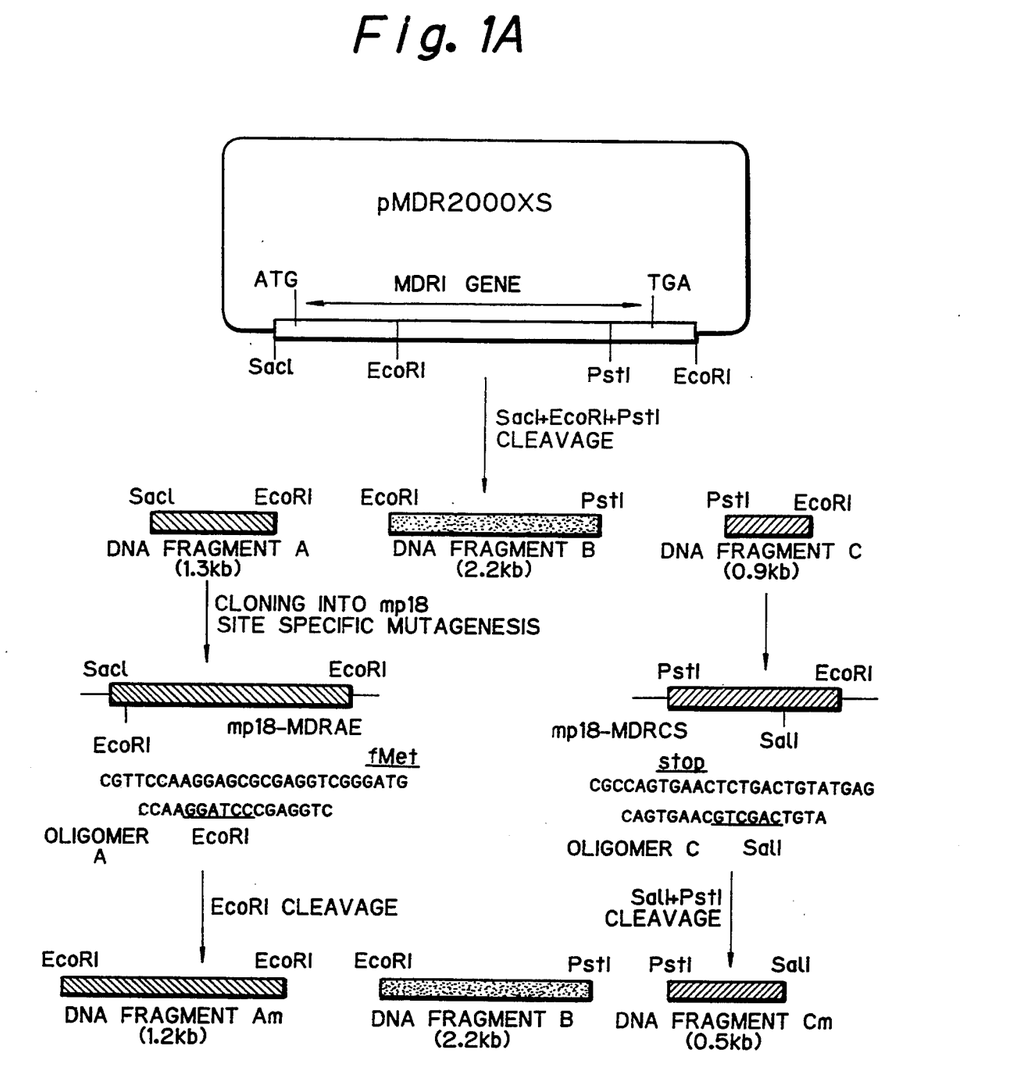
FIG. 1A illustrates a process for preparing DNA fragments Am, B and Cm employed for the preparation of recombinant plasmids pYM1 and pYM2 which are constructed for the expression of the MDR gene in yeast.

Preparation of Restriction Sites for MDR1 Gene (FIG. 1A)

Plasmid pYMDR2000XS [I. Pastan, et al., Proc. Natl. Acad. Sci. USA, 85, 4486–4490 (1988)] including the full length of the cDNA of MDR1 gene was cleaved with restriction enzymes SacI, EcoRI and PstI. Thus, a DNA fragment A of 1.3 kb including the initiator codon ATG of MDR1 gene, a DNA fragment C including the terminator codon TGA and a DNA fragment B located between the fragments A and C were obtained. The DNA fragments A and C were respectively inserted between the EcoRI and SacI sites and the EcoRI and PstI sites of phage M13mp18 to give recombinant phages. From these recombinant phages, an EcoRI site was formed immediately before the initiator codon of MDR1 gene and a SalI site was formed immediately after the terminator codon thereof by a site-specific mutagenesis. This site-specific mutagenesis was performed in the following manner with the use of the kit MUTA-GENE (manufactured by Bio-Rad Co.) which was prepared in accordance with Kunkel's method [Kunkel, T. A., Proc. Natl. Acad. Sci. USA, 82, 488 (1985)].

First, the recombinant phages obtained above were respectively introduced into E. coli CJ236 which incorporates uracil instead of thymine, to give recombinant phages, respectively, carrying a DNA wherein thymlne was substituted with uracil. Next, the single-stranded DNA prepared from said respective phages was paired with an appropriate oligonucleotide synthesized for the preparation of the above-mentioned restriction sites. Thus, a double-stranded DNA was formed following to the reaction with T4DNA polymerase and T4DNA ligase. The pairing and the enzymatic reaction were conducted under the conditions recommended by the producer of the kit. As the synthetic oligonucleotides for the preparation of the restriction sites, oligomer A (5'-GAGCGCGAATTCGGGATG-3') was employed for the preparation of an EcoRI site, while oligomer C (5'-CAGTGAACGTCGACTGTA-3') was employed for the preparation of a SalI site. Oligomer A was paired with the single-stranded phage DNA including the aforesaid DNA fragment A. On the other hand, oligomer C was paired with the single-stranded DNA including the aforesaid DNA fragment C.

Then E. coli MV1190 was transformed with the respective double-strands thus obtained and the double-stranded DNAs were propagated from the phage clones thus obtained. It was confirmed that the respective double-stranded DNAs had an EcoRI site and a SalI site. The phage wherein the EcoRI site was formed was named mp18-MDRAE, while the one wherein the SalI site was formed was named mp18-MDRCS.

E. coil MV1190 strain used above is a wild strain corresponding to E. coli CJ236. Reasons for the selection of these strains are as follows. The phage DNA produced in CJ236 contained uracil instead of thymlne and thus could not be propagated in the wild strain MV1190. Thus, the site-specific mutagenesis could be efficiently performed by transforming MV1190 with the use of the phage single-stranded DNA, which had been grown in CJ236 and thus contained uracil, as a template to be paired with the oligomer.

Example 2

Figure 1B:
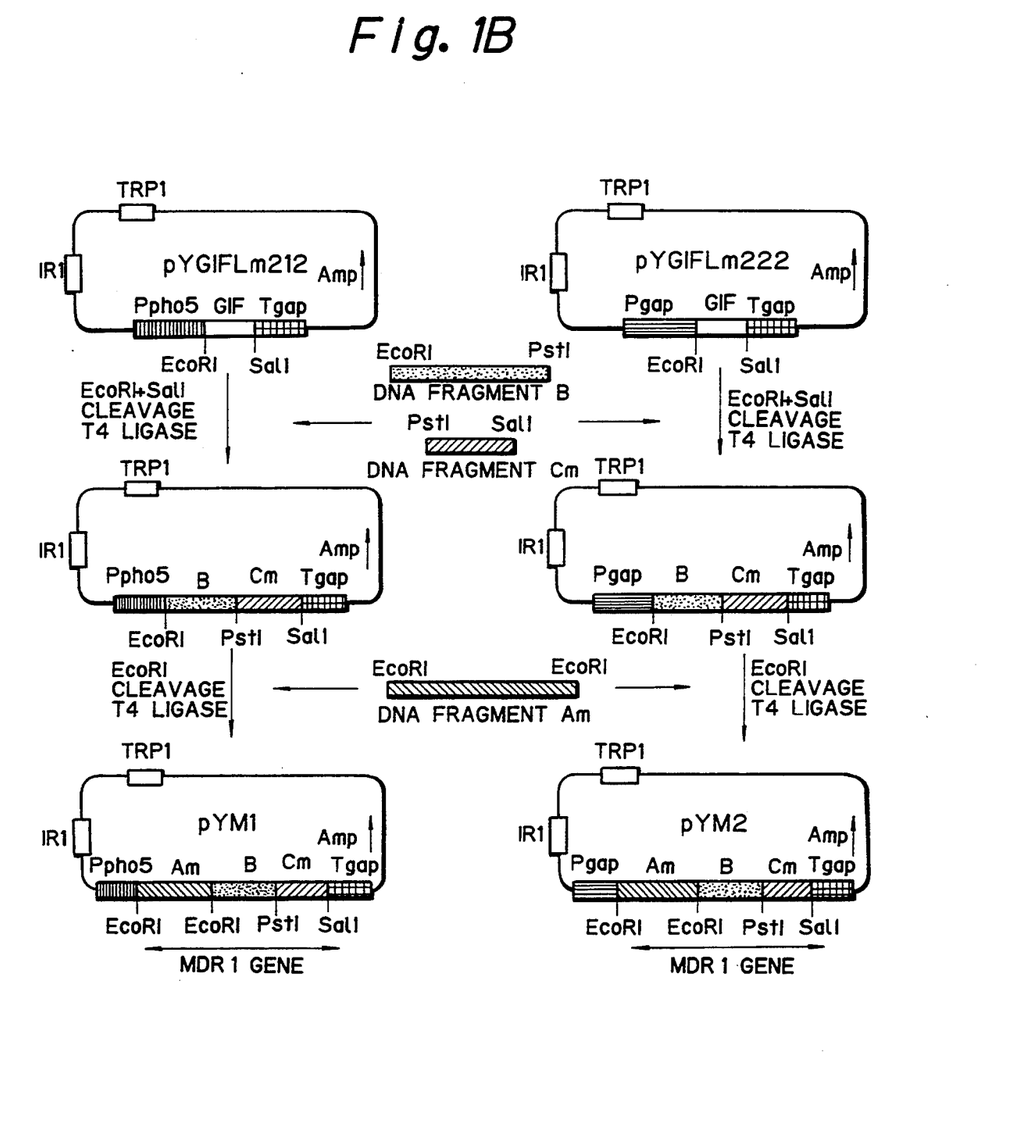
FIG. 1B illustrates a process for preparing the recombinant plasmids pYM1 and pYM2 by using the DNA fragments Am, B and Cm.

Preparation of an Yeast Expressing MDR Gene (FIG. 1B)

The double-stranded DNA of the phage mp18-MDRAE was cleaved with EcoRI and thus a 1.2 kb DNA fragment Am was collected. On the other hand, the double-stranded DNA of the phage mp18-MDRCS was cleaved with PstI and SalI and thus a 0.5 kb DNA fragment Cm was collected. These DNA fragments Am and Cm and the aforesaid DNA fragment B were used in the construction of an expression vector for the expression of human MDR1 gene. The expression vector was prepared from plasmids pYGIFLm212 and pYGIFLm222. These plasmids are disclosed in Japanese Patent Laid-Open No. 141888/1986. pYGIFLm212 is a YEp type vector which includes IR1 (a replication origin from 2 μm DNA) required for the replication in yeast to take place, a TRP1 (a selection marker in yeast), Amp (a selection marker in E. coli) and a DNA fragment wherein a human γ-interferon gene has been inserted between the acid phosphatase promoter (Ppho5) of yeast origin and the glyceraldehyde-3-phosphate dehydrogenase terminator (Tgap) of yeast origin at the EcoRI and SalI sites. On the other hand, pYGIFLm222 has the same construction as that of pYGIFLm212 except that the promoter Ppho5 in pYGIFLm212 is replaced by a glyceraldehyde-3-phosphate dehydrogenase promoter (Pgap). These plasmids pYGIFLm212 and pYGIFLm222 were cleaved with EcoRI and SalI to give vector DNA fragments of 8.0 kb and 8.3 kb, respectively.

The DNA fragment (8.0 kb) in the vector portion of pYGIFLm212 was ligated to DNA fragment B and Cm with T4DNA ligase. Then E. coli strain DHS, which is a host showing a high transformation efficiency, was transformed with the ligated fragment. Thus, a plasmid comprising the DNA fragments B and Cm which were bound after Ppho5 in this order was obtained. This plasmid was cleaved with EcoRI and a DNA fragment Am was inserted in such an orientation that the initiation codon was located immediately after the promoter Ppho5. The plasmid thus obtained was referred to as pYM1. pYM1 comprised DNA fragments Am, B, Cm and Tgap after Ppho5 in this order.

Similarly, plasmid pYM2 was prepared from the 8.3 kb DNA fragment of pYGIFLm222. pYM2 comprised DNA fragments Am, B, Cm and Tgap after Pgap in this order.

A yeast strain *Saccharomyces cerevisiae* G-1315 (α, trp1) was transformed with pYM1 and pYM2, respectively. The yeast strain used is disclosed by Japanese Patent Laid-Open No. 245664/1988 (Japanese Patent Application No. 078301/1987). The yeast strain 8-1315 containing plasmid pYM1 was named *Saccharomyces cerevisiae* SAM 1323 and has been deposited under the Budapest Treaty with the Fermentation Research Institute, Agency of Industrial Science and Technology as FERM BP-2749.

Example 3

Confirmation of Expression of the MDR Gene in the Transformed Yeasts

The respective yeast strains G-1315(pYM1) and G-1315(pYM2) were cultured in 5 ml of a YNBD medium [prepared by adding 2% of glucose to Yeast Nitogen Base (Difco)] overnight under shaking at 30° C. In the case of G-1315 which was free from the recombinant plasmids and was employed as a control, 30 μg/ml of tryptophan was added (the same will apply hereinafter). 0.5 ml of each culture medium was transplanted into 10 ml of a BHhigh medium [Burkholder's medium, Bull. Torvey Botan. Club., 70, 312 (1943)] and cultivated therein for 5 hours under shaking at 30° C. Two kinds of BH mediums, a low phosphoric acid medium (BHlow medium) and a high phosphoric acid medium (BHhigh medium) were used. Next, the cells were centrifuged and washed with aseptic water. Then these cells were incubated in 10 ml portions of BHlow medium or BHhigh medium for 3 hours under shaking at 30° C. The cells were centrifuged and washed with aseptic water. Then, these cells were suspended in 1 ml of a zymolyase solution [0.2 mg/ml Zymolyase 100T (manufactured by Seikagaku Kogyo)—1M sorbitol—50 mM potassium phosphate buffer solution (pH 7.0)—14 mM 2-mercaptoethanol] and maintained at 30° C. for 30 minutes to allow the formation of protoplasts. Then, the protoplasts were centrifuged and washed with 3 ml of a sorbitol buffer solution [1M sorbitol—50 mM potassium phosphate buffer solution (pH 7.0)]. Then, they were suspended in 1 ml of a 50 mM potassium phosphate buffer solution (pH 7.0) containing 0.14 of Triton X-100 and allowed to stand at 0° C. for 30 minutes to cause lysls of the protoplasts. The lysate was then centrifuged at 15,000 rpm for 15 minutes. The precipitate thus obtained was collected as a membrane fraction, while the supernatant was collected as a cytoplasmic fraction. The precipitate was suspended in 100 μl of Ring's buffer solution [Debenham, P. G., Mol. Cell. Biol., 2, 881 (1982): a buffer solution for denaturing proteins in SDS-PAGE of, for example, membrane proteins], while the supernatant was ixed with an equal amount of Ring's buffer solution of the double concentration and heated to 100° C. for 5 minutes. The insoluble matters thus formed were removed by centrifuging and the supernatant was mixed with an equal amount of a urea solution (refer to Debenham P. G., supra).

The proteins in the sample thus obtained were analyzed by SDS-polyacrylamide gel electrophoresis at a gel concentration of 7.54. After the completion of the electrophoresis, the separated proteins were transferred onto a nitrocellulose film by the blotting apparatus manufactured by Biometra Co. The film was immersed in a TBS buffer solution [20 mM tris-HCl (pH 7.6)—137 mM NaCl] containing 5% of calf serum for 30 minutes and then washed with the TBS buffer solution. The washed film was then allowed to stand in 20 ml of the TBS buffer solution containing 40 μl of anti-P-glycoprotein monoclonal antibody C219 (manufactured by Centocor Co.) and 5% of calf serum at 4° C. overnight. The nitrocellulose film was thoroughly washed with the TBS buffer solution and then allowed to stand overnight in 20 ml of the TBS buffer solution containing 40 μl of an antimouse IgG antibody labelled with peroxidase (manufactured by Bio-Rad Co.) and 5% of calf serum at room temperature. After thoroughly washing with the TBS buffer solution, the color of protein bands reacting with the anti-P-glycoprotein antibody was allowed to develop in the TBS buffer solution containing 4-chloro-1-naphthol and hydrogen peroxide.

Figure 2:
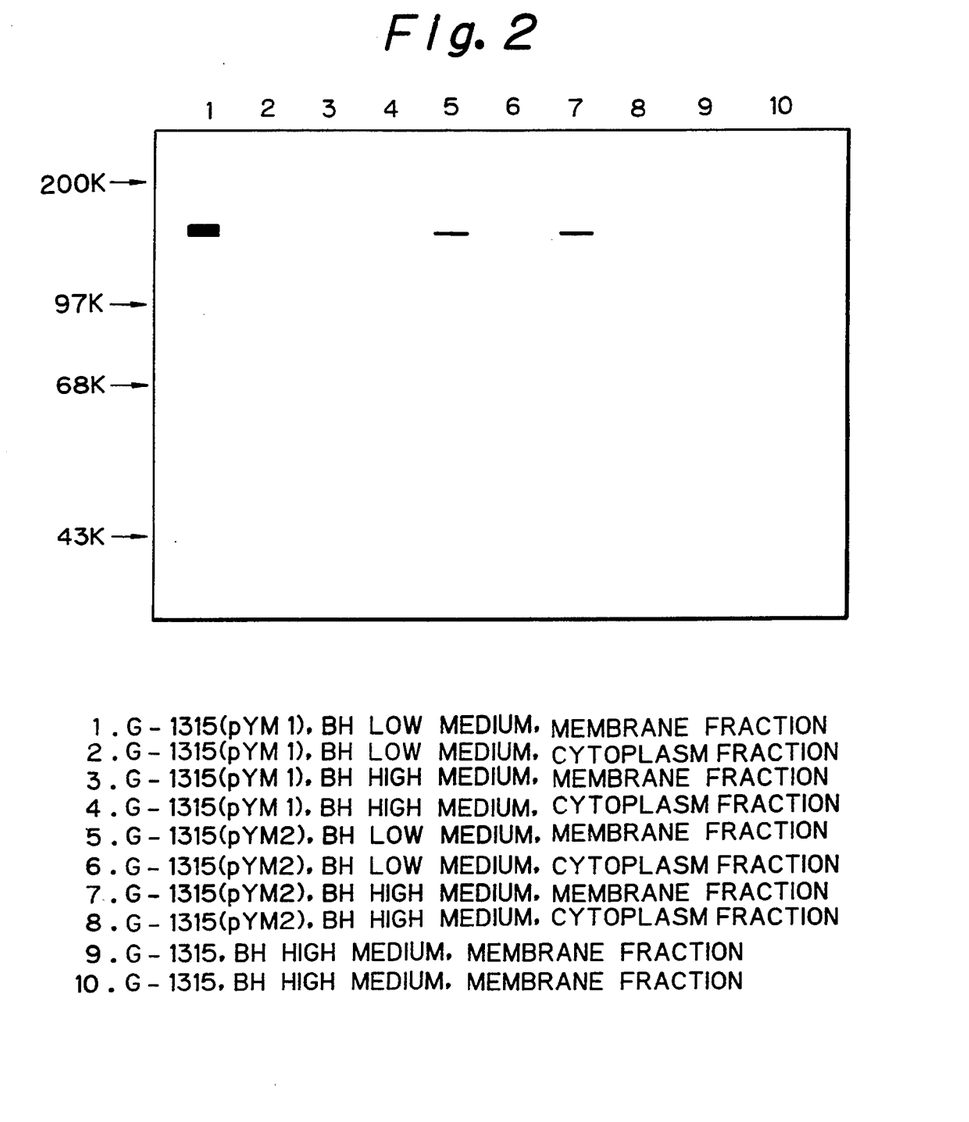
FIG. 2 is an illustration of the reaction with a monoclonal antibody performed to prove the fact that the P-glycoprotein produced by the MDR gene expression yeast exists at the cell membrane.

As FIG. 2 shows, the membrane fraction of the recombinant yeast G-1315(pYM1) grown in BHlow medium showed an intense band corresponding to P-glycoprotein of 170 kd. On the other hand, the supernatant fraction showed no such protein band. Further, neither the membrane fraction of said yeast grown in BHhigh medium nor the supernatant fraction thereof showed the same band.

On the other hand, the recombinant yeast G-1315(pYM2) gave a weak band at 170 kd in the membrane fraction both when grown in BHhigh medium or in BHlow medium but the supernatant fraction did not give the band in each case. The membrane fraction of the recombinant plasmid-free G-1315 strain gave no band corresponding to P-glycoprotein.

These results indicate that MDR1 gene was expressed in yeast cells and the gene product thereof (namely, P-glycoprotein) was accumulated in the membrane fraction of yeast. It is suggested, furthermore, that the expression of MDR1 gene in yeast cells with the use of Ppho5, which would cause inductive expression, is more remarkable than the expression thereof with the use of Pgap, which would cause a constitutive expression.

Example 4

Preparation of Membrane Fraction by MDR Expression Yeast

A membrane fraction wherein P-glycoprotein was concentrated was prepared from yeast strain G-1315(pYM1) grown in BHlow medium. The membrane fraction was prepared in the following manner in accordance with the method reported by Gerald et al. [Gerald, F. et al., J. Biol. Chem., 258, 7911–7914 (1983)]. The recombinant yeast strain G1315(pYM1) was incubated in 5 ml of a YNBD medium overnight under shaking at 30° C. 1 ml of the culture medium was added to 200 ml of BHhigh medium and incubated therein at 30° C. for 24 hours. The cells were collected by centrifuging and suspended in 400 ml of BHlow medium, followed by incubating therein at 30° C. for 5 hours. The cells were centrifuged, washed with aseptic water and suspended in 20 ml of a zymolyase solution, which is an enzyme frequently employed for lysing yeast cell walls so as to form protoplasts. After being maintained at 30° C. for 30 minutes, protoplasts were formed. The protoplasts were centrifuged and washed with a sorbitol buffer solution. Then they were suspended in 20 ml of buffer solution A [50 mM EPES (pH 7.2)—1 mM MgCl$_2$—0.1 mM EDTA—0.2 mM pAPMSF {(p-aminodiphenyl)methanesulfonyl fluoride): used as a protease inhibitor for preventing the decomposition of P-glycoproteln}] containing 0.1% of Triton X-100 and maintained at 0° C. for 30 minutes to lyse the protoplasts. The suspension was then centrifuged at 120×g for 10 minutes. After removing the precipitate, the supernatant was further centrifuged at 27,000×g for 15 minutes. Thus, the membrane fraction was collected as the precipitate. The precipitate was suspended in buffer solution A containing 10% of glycerol and stored at −80° C.

Figure 3:
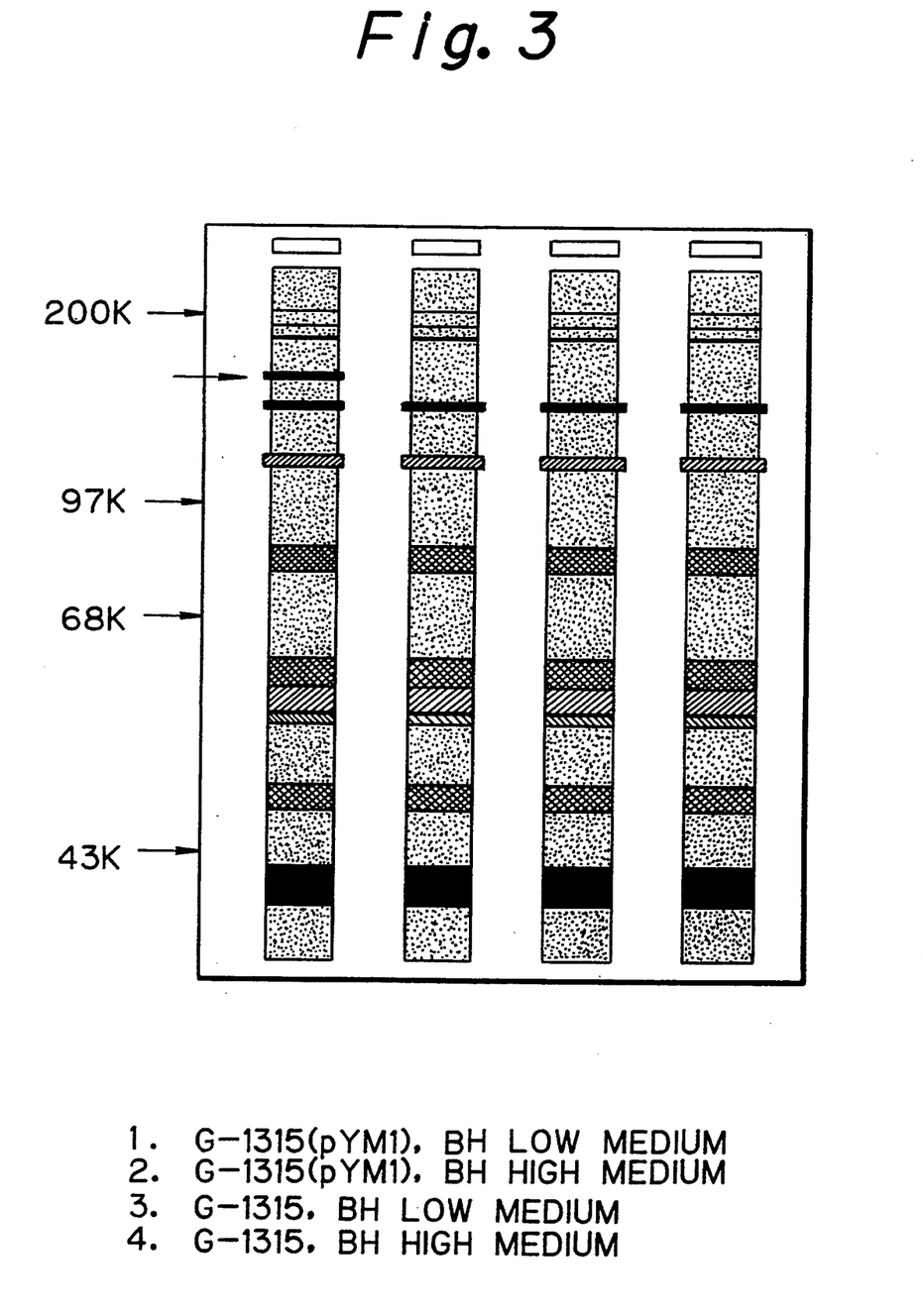
FIG. 3 is an illustration of the electrophoresis which indicates that P-glycoprotein is concentrated in the cell membrane fraction prepared from the MDR gene expression yeast.

The membrane fraction thus prepared was subjected to SDS-polyacrylamlde gel electrophoresis to separate the proteins. Then the protein bands were detected by staining with Coomassie blue. As FIG. 3 shows, the membrane fraction of the recombinant yeast G-1315(pYM1) grown in BHlow medium showed a band of 160–170 kd corresponding to P-glycoprotein. However, G-1315 strain (pYM1) grown in BHhigh medium and the G-1315 strain free from any recombinant plasmid showed no such protein band. Since the membrane fraction prepared by the method described in Example 3 showed no such band, it could be confirmed that the expressed P-glycoprotein was concentrated in the membrane fraction prepared by the method described herein. The membrane fraction of the MDR gene expression yeast thus prepared contained P-glycoprotein in the same state as it is present in multidrug-resistant cells and hence would be employable as an antigen for preparing a monoclonal antibody to be used for the evaluation of multidrug resistance.

Example 5

Functional Analysis of P-Glycoprotein Expressed in Yeast by Binding Assay

By using the membrane fraction of the MDR expression yeast prepared by the method described in Example 4, the ability of the P-glycoproteln expressed in yeast cells in binding to azldopine was examined by a binding assay. The binding assay was performed in the following manner in accordance with the method reported by A. R. Safa et al. [A. R. Safa et al., J. Biol. Chem., 262, 7884–7888 (1987)].

Figure 4:
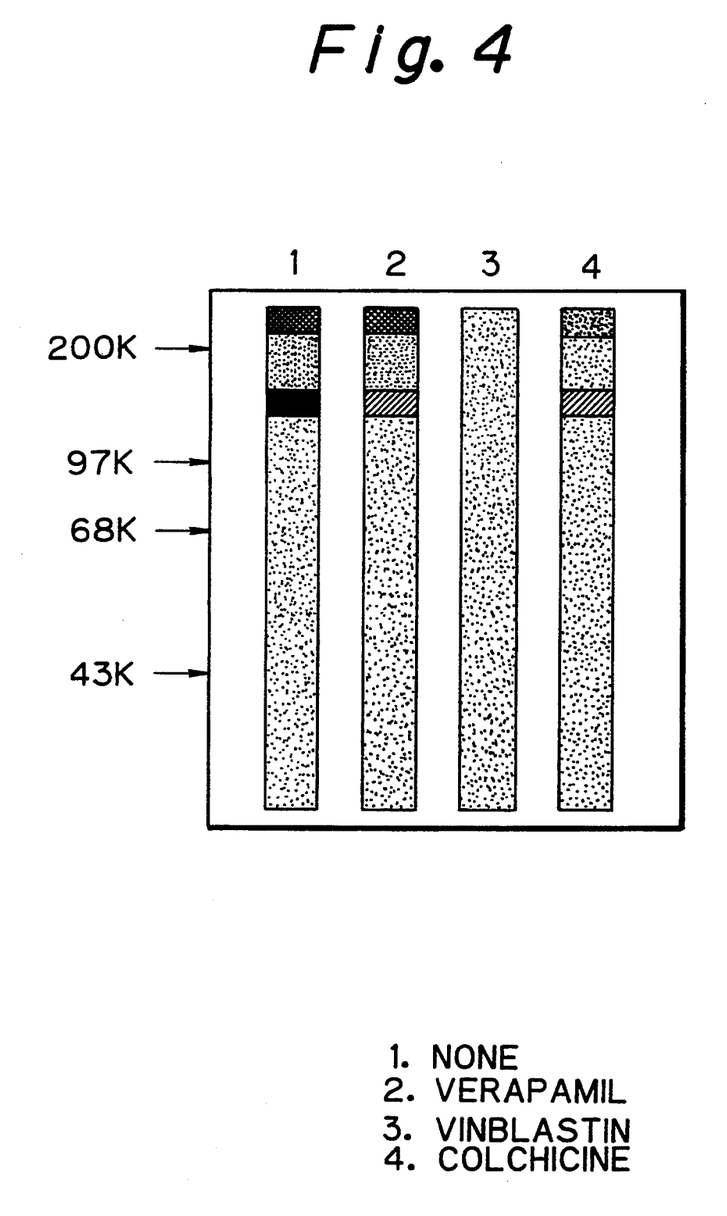
FIG. 4 is an illustration showing the results of a binding assay of the cell membrane fraction of the MDR gene expression yeast.

1 μl of the membrane fraction prepared by the method described in Example 4 and 0.5 μl of $^3$-H-azidopine (manufactured by Amersham) were mixed together and maintained at 37° C. for an hour. Then the mixture was irradiated with ultraviolet light of 302 nm in an ice bath for 5 minutes. The membrane fraction was washed with buffer solution A containing 1% of Triton X-100, treated with Ring's buffer solution and the urea buffer solution in the same manner as the one described in Example 3 and then subjected to SDS-polyacrylamide gel electrophoresis. After the completion of the electrophoresis, the gel was dried and treated with the enhancer for the autoradiography which followed. As FIG. 4 shows, a band of 160 to 170 kd corresponding to P-glycoprotein was observed. This band disappeared or faded in the presence of verapamil, vinblastin and colchicine in the reaction mixture. These results indicate that the P-glycoprotein expressed in yeast can bind to azidopine. It is indicated, furthermore, that the bindability to azidopine of the p-glycoprotein expressed in yeast is inhibited by adding an excessive amount of verapamil, which is known to inhibit the drug excretion function of P-glycoprotein or vinblastin and colchicine, each known to be excreted by the action of P-glycoproteln. Thus it is suggested not only that the P-glycoprotein expressed in yeast is contained in the membrane fraction but also that said P-glycoprotein exerts a function in yeast cells which is comparable to the drug-excretion function observed in animal resistant cells. Accordingly, screening of drugs capable of overcoming multidrug resistance will be achieved with the use of the membrane fraction of the yeast wherein the aforesaid P-glycoprotein has been concentrated.

The present invention is useful in screening drugs capable of overcoming multidrug resistance of cancer cells, in evaluating the degree of the multidrug resistance of cancer cells and in preparing an antibody for P-glycoprotein required for overcoming multidrug resistance, in the field of medicine, in particular, in chemotherapy for cancer.

More particularly, the present invention makes it possible to solve the following problems by expressing MDR-related genes in yeast and using said MDR gene expression yeast or the membrane fraction containing a substantial amount of P-glycoprotein prepared from said yeast and, furthermore, by using the drug-binding ability of the aforesaid membrane fraction:

(1) In order to overcome the multidrug resistance of cancer cells, it is required to clarify the multidrug resistance mechanism of said cancer cells in detail. The MDR gene expression yeast of the present invention is useful as a multidrug resistance model for achieving this object.

(2) Screening of drugs capable of overcoming the multidrug resistance of cancer cells by inhibiting the drug-excretion function of P-glycoprotein can be easily performed by using the MDR gene expression yeast of the present invention or a membrane fraction prepared from said yeast.

(3) A monoclonal antibody to P-glycoprotein can be easily prepared by using the MDR gene expressed yeast of the present invention or a membrane fraction prepared therefrom as an antigen.

Although a yeast host, which is an eukaryote similar to that found in man and animals, has cells closely similar to animal cells in the structure and function, it is a microorganism and thus a large amount of yeast cells can be easily grown within a short period, without suffering from any problems observed in the culture of animal cells. Furthermore, a great amount of genetic and biochemical knowledge on yeasts is available and the gene recombination techniques required for introducing heterologous genes and expressing them (for example, vectors, promoters and transformation techniques) have been already established.

Therefore, yeast cells wherein MDR gene is expressed on the cell surface can be easily grown. It is considered, furthermore, that said yeast cells have a smaller number of antigen determinants on the cell surface, compared with animal cells. Thus the yeast is suitable as an antigen for preparing an antibody for P-glycoprotein.

What is claimed is:

1. A transformed strain of the yeast *saccharomyces cerevisiae* having P-glycoprotein accumulated in the cell membrane wherein said yeast has been transformed with a recombinant vector comprising a first DNA fragment consisting essentially of MDR1 gene, a second DNA fragment consisting essentially of PHO5 promoter located upstream of said MDR1 gene, and a third DNA fragment consisting essentially of a yeast GAP terminator located downstream of said MDR1 gene in such a manner as to allow expression of said MDR1 gene in said yeast cell.

2. The transformed yeast as claimed in claim 1, wherein said MDR1 gene is derived from human KB cells.

3. The transformed strain as claimed in claim 1, wherein said strain is *Saccharomyces cerevisiae* G-1315 (FERM BP-2749).

4. The transformed yeast as claimed in claim 1, wherein the P-glycoprotein accumulated in the cell membrane of said yeast is capable of binding to azidopine.

5. A composition comprising the cell membranes of said transformed strain of claim 1 and a buffer, wherein P-glycoprotein is accumulated in said cell membranes.

6. A method of screening multidrug-resistant antagonists which comprises screening substances capable of inhibiting the binding of azidopine to the P-glycoprotein in the cell membranes of the composition of claim 5.

7. A method of screening multidrug-resistant antagonists which comprises screening substances capable of inhibiting the binding of azidopine to the P-glycoprotein in the cell membrane of the transformed yeast of claim 1.

8. A method of screening multidrug-resistant antagonists which screening substances capable of inhibiting the binding of azidopine to the P-glycoprotein in the cell membrane of the transformed yeast of claim 4.

* * * * *